United States Patent
Stewart

(10) Patent No.: US 9,918,813 B2
(45) Date of Patent: Mar. 20, 2018

(54) DENTAL PRODUCTS AND PROCEDURES

(71) Applicants: BAY MATERIALS LLC, Menlo Park, CA (US); Ray F. Stewart, Menlo Park, CA (US)

(72) Inventor: Ray F Stewart, Redwood City, CA (US)

(73) Assignee: BAY MATERIALS LLC, Fremont, CA (US)

( * ) Notice: Subject to any disclaimer, the term of this patent is extended or adjusted under 35 U.S.C. 154(b) by 0 days.

(21) Appl. No.: 14/381,202

(22) PCT Filed: Feb. 27, 2013

(86) PCT No.: PCT/US2013/027950
§ 371 (c)(1),
(2) Date: Aug. 26, 2014

(87) PCT Pub. No.: WO2013/130552
PCT Pub. Date: Sep. 6, 2013

(65) Prior Publication Data
US 2015/0374464 A1    Dec. 31, 2015

Related U.S. Application Data

(60) Provisional application No. 61/634,370, filed on Feb. 27, 2012.

(51) Int. Cl.
*A61C 13/08* (2006.01)
*A61C 7/08* (2006.01)
(Continued)

(52) U.S. Cl.
CPC .............. *A61C 13/082* (2013.01); *A61C 7/08* (2013.01); *A61K 6/0005* (2013.01); *B32B 27/20* (2013.01);
(Continued)

(58) Field of Classification Search
CPC ........ A61K 6/0008; A61C 13/082; A61C 7/08
(Continued)

(56) References Cited

U.S. PATENT DOCUMENTS 3,936,939 A    2/1976  Faunce
3,986,261 A   10/1976  Faunce
(Continued)

FOREIGN PATENT DOCUMENTS

JP    11-128249    5/1999
RU    217-3471     8/1996
(Continued)

OTHER PUBLICATIONS

International Search Report and Preliminary Opinion on PCT/US 2013/027950.
(Continued)

*Primary Examiner* — Nicholas Lucchesi
(74) *Attorney, Agent, or Firm* — T.H.P. Richardson

(57) ABSTRACT

Polymeric shells which fit over natural teeth to change the perceived color of the teeth, and optionally to provide orthodontic support. The shells are prepared by thermoforming selected polymeric sheets which contain optical additives; the optical additives cause the combination of the shell and the teeth to have a desired appearance. The shell preferably has transparency of greater than 75%, particularly greater than 85%.

12 Claims, 1 Drawing Sheet

(51) Int. Cl.
  *A61K 6/00*    (2006.01)
  *B32B 27/20*   (2006.01)
  *C08L 67/02*   (2006.01)
  *C09K 11/06*   (2006.01)
  *B29L 31/00*   (2006.01)
  *B29C 51/12*   (2006.01)

(52) U.S. Cl.
  CPC .............. *C08L 67/02* (2013.01); *C09K 11/06* (2013.01); *B29C 51/12* (2013.01); *B29L 2031/7536* (2013.01)

(58) Field of Classification Search
  USPC .................................. 433/6, 215, 217.1, 229
  See application file for complete search history.

(56) References Cited

U.S. PATENT DOCUMENTS

| | | | |
|---|---|---|---|
| 4,032,627 A | 6/1977 | Santucci | |
| 4,361,528 A * | 11/1982 | Ginsburg | A61C 9/0006 264/157 |
| 4,433,959 A * | 2/1984 | Faunce | A61C 5/00 106/35 |
| 4,512,743 A | 5/1985 | Corbett | |
| 4,527,975 A | 7/1985 | Gharafi et al. | |
| 4,650,418 A * | 3/1987 | Blair | A61C 13/0003 433/203.1 |
| 5,693,313 A | 12/1997 | Shiraishi | |
| 5,716,208 A | 2/1998 | Forman | |
| 5,763,049 A | 6/1998 | Frey et al. | |
| 5,951,291 A | 9/1999 | Albert et al. | |
| 5,975,893 A | 11/1999 | Chishti et al. | |
| 6,036,494 A * | 3/2000 | Cohen | A61C 5/00 433/215 |
| 6,210,163 B1 * | 4/2001 | Cohen | A61C 5/00 106/35 |
| 6,210,363 B1 | 4/2001 | Cohen | |
| 6,343,933 B1 | 2/2002 | Montgomery | |
| 6,368,576 B1 | 4/2002 | Jensen | |
| 6,444,725 B1 | 9/2002 | Trom | |
| 6,461,158 B1 * | 10/2002 | Sagel | A45D 44/005 359/884 |
| 6,503,485 B1 | 1/2003 | Allred | |
| 6,537,360 B2 | 3/2003 | Miyami | |
| 6,986,883 B2 | 1/2006 | Pellico | |
| 7,118,732 B2 | 10/2006 | Ibrahim | |
| 7,156,637 B1 * | 1/2007 | Kutsch | A61C 13/206 264/17 |
| 7,210,926 B2 | 5/2007 | Tadros et al. | |
| 7,214,262 B2 | 5/2007 | Hurwitz et al. | |
| 7,220,122 B2 | 5/2007 | Chishti | |
| 7,357,637 B2 | 4/2008 | Liechtung | |
| 7,476,697 B2 | 1/2009 | Patacca | |
| 2002/0006600 A1 | 1/2002 | Cohen | |
| 2002/0192617 A1 | 12/2002 | Phan | |
| 2003/0133884 A1 | 7/2003 | Chang | |
| 2003/0138757 A1 | 7/2003 | Cohen et al. | |
| 2003/0162863 A1 * | 8/2003 | Satoh | A61K 6/0052 523/109 |
| 2003/0194382 A1 * | 10/2003 | Chang | A61K 8/0208 424/53 |
| 2004/0136927 A1 * | 7/2004 | Kim | A61C 19/066 424/53 |
| 2004/0138082 A1 | 7/2004 | Sugihara | |
| 2005/0003318 A1 * | 1/2005 | Choi | A61C 7/00 433/6 |
| 2005/0100853 A1 | 5/2005 | Tadros | |
| 2005/0143274 A1 | 6/2005 | Ghosh | |
| 2005/0172429 A1 | 8/2005 | Russell et al. | |
| 2005/0175552 A1 | 8/2005 | Hoic | |
| 2005/0179952 A1 | 8/2005 | Hoic | |
| 2005/0287084 A1 | 12/2005 | Ibrahim et al. | |
| 2006/0024245 A1 | 2/2006 | Gebreselassie | |
| 2006/0073433 A1 | 4/2006 | Anderson | |
| 2006/0104922 A1 | 5/2006 | Tarver | |
| 2006/0177792 A1 * | 8/2006 | Touchstone | A61C 13/0004 433/26 |
| 2006/0292088 A1 | 12/2006 | Maitra | |
| 2007/0086960 A1 | 4/2007 | Tarver | |
| 2007/0298381 A1 * | 12/2007 | Collodoro | A61C 5/002 433/215 |
| 2008/0160193 A1 * | 7/2008 | Mitchell | A61C 13/0003 427/255.19 |
| 2008/0193899 A1 | 8/2008 | Karlsson | |
| 2008/0254406 A1 * | 10/2008 | Wagner | A61C 9/0006 433/41 |
| 2008/0303181 A1 | 12/2008 | Holland | |
| 2009/0035714 A1 | 2/2009 | Kuo | |
| 2009/0035716 A1 | 2/2009 | Trimmer | |
| 2009/0130624 A1 * | 5/2009 | Sun | A61F 5/566 433/48 |
| 2009/0155190 A1 | 6/2009 | Gebreselassie | |
| 2010/0081728 A1 * | 4/2010 | Uchida | A61K 6/0094 523/105 |
| 2010/0323317 A1 | 12/2010 | Cosse | |
| 2011/0129786 A1 | 2/2011 | Chun et al. | |
| 2011/0143302 A1 | 6/2011 | Dellinger | |
| 2011/0171145 A1 | 7/2011 | Caldwell | |
| 2011/0200971 A1 * | 8/2011 | Kalgutkar | A61K 6/0017 433/201.1 |
| 2011/0236323 A1 | 9/2011 | Speronello et al. | |
| 2011/0256509 A1 | 10/2011 | Russell et al. | |
| 2014/0072926 A1 | 3/2014 | Valoir | |
| 2014/0295376 A1 * | 10/2014 | Uchida | A61C 13/082 433/203.1 |

FOREIGN PATENT DOCUMENTS

| | | |
|---|---|---|
| WO | WO 2006/009745 | 1/2006 |
| WO | WO 2007/021840 | 2/2007 |
| WO | WO 2011/143620 | 11/2011 |

OTHER PUBLICATIONS

Office Action on JP App 2014-558958.
Office Action and Search Report on EP 13754394.8.
Office Action on CN 201380016401.

\* cited by examiner

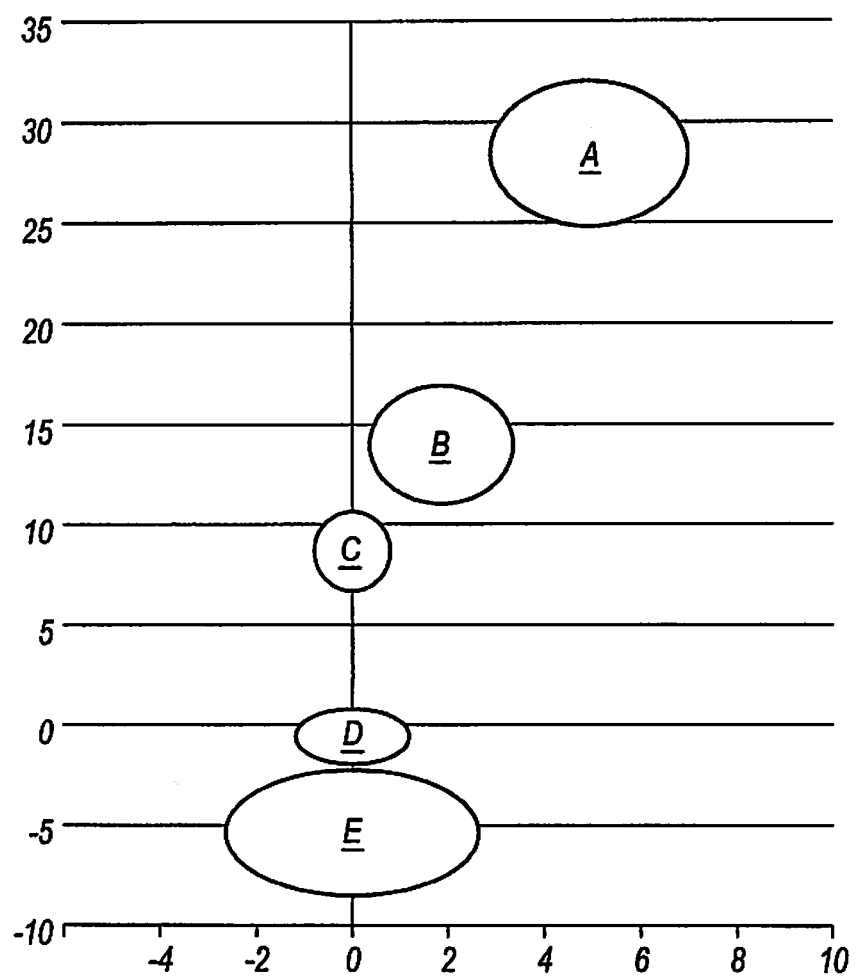

DENTAL PRODUCTS AND PROCEDURES

CROSS-REFERENCE TO RELATED APPLICATIONS

This application is an application under 35 USC 371 based on PCT/US 2013/027950, filed Feb. 27, 2013, and claims priority from U.S. Provisional Application 61/634370, filed Feb. 27, 2012. The entire disclosure of each of those applications is incorporated herein by reference for all purposes.

FIELD OF THE INVENTION

This invention relates to products and procedures for changing the appearance of teeth.

BACKGROUND OF THE INVENTION

Many products and procedures have been used, or proposed for use, in order to change or modify teeth in the human mouth. In orthodontic procedures, the objective is to change the relative positions of two or more teeth. In some cosmetic procedures, the objective is to change the perceived color of teeth so that the teeth appear whiter.

One orthodontic procedure makes use of one or more rigid polymeric shells each of which fits over the teeth and, when in place, does not fit precisely to one or more of the teeth and, therefore, imparts a displacing force to the teeth and over the course of time changes the relative positions of two or more teeth. Reference may be made for example to U.S. Pat. No. 5,975,893 (Chishti) and U.S. Pat. No. 7,220,122 (Chishti), the entire disclosure of each of which is incorporated herein by reference. Many polymers, including some of those used in dental and orthodontic applications, have a slightly yellow color which is produced during manufacturing or processing such as extrusion, injection molding and/or thermoforming. Consequently, although the primary objective of the rigid polymeric shell is functional, it often contains a small quantity of additives to change the yellow color. This is referred to as "color compensation" or "color correction".

Much effort and expense has been expended in order to whiten teeth. However, the known cosmetic procedures have substantial disadvantages. Many cosmetic procedures make use of bleaching agents which are applied directly to the teeth; bleaching agents can damage the natural tooth structure itself and/or can produce different cosmetic effects on the natural tooth structure and/or stains and/or fillings and/or crowns. Other cosmetic procedures make use of compositions which form a coating on top of the teeth; those compositions are difficult to apply uniformly and accurately, and degrade relatively rapidly and/or are difficult to remove. For information about known cosmetic procedures, reference may be made for example to U.S. Pat. Nos. 3,986,261, 4,032,627, 5,716,208, 6,343,933, 6,368,576, 6,503,485, 6,986,883 and 7,214,262, and US Patent Publications 2005/0175552 and 2007/0086960, the entire disclosure of each of which is Incorporated herein by reference for all purposes

SUMMARY OF THE INVENTION

I have discovered, in accordance with the present invention, new products and procedures for changing the perceived color of teeth. In some embodiments of the invention, the products and procedures also change the relative positions of two or more teeth. Throughout this specification, the terms tooth and teeth includes natural teeth, including natural teeth which have been modified by fillings or by crowns, implanted teeth, artificial teeth that are part of a bridge or other fitting secured to one or more natural or implanted teeth, and artificial teeth that are part of a removable fitting.

In a first aspect, this invention provides a self-supporting shell which fits over one or more teeth and which is composed of a polymeric composition comprising a polymer and one or more optical additives which cause the combination of the shell and the teeth to have a desired appearance. The term "optical additive" is used herein to mean an additive which substantially changes the color or light transmission properties of the polymeric composition.

In a second aspect, this invention provides a method of providing a desired change in the appearance of teeth which comprises placing a self-supporting shell according to the first aspect of the invention over one or more teeth.

In a third aspect, this invention provides a method of making a self-supporting shell according to the first aspect of the invention, the method comprising forming a selected polymeric composition into a shape which will fit over the teeth over which the shell is to be placed, the selected polymeric composition preferably having been selected by assessing the color of the teeth over which the shell is to be fitted and, based on that assessment, selecting the polymeric composition from a range of polymeric compositions of different colors.

In a fourth aspect, this invention provides a method which comprises (A) assessing the color of teeth over which a self-supporting shell according to the first aspect of the invention is to be placed, (B) selecting from a range of compositions having different colors, a composition which will provide a desired change in the appearance of teeth when formed into a self-supporting shell according to the first aspect of the invention, and (C) forming the selected composition into a self-supporting shell.

In a fifth aspect, this invention provides a method which comprises (A) selecting, from a set of colored samples, a sample which matches the color of teeth to be treated, and (B) correlating the selected sample with a polymeric composition which, when formed into a self-supporting shell and placed over the teeth will give the teeth a desired appearance.

In a sixth aspect, this invention provides a sheet of a polymeric composition for use in the method of the third or fifth aspect of the invention, for example by thermoforming the sheet around a physical model of the teeth over which the shell is to be fitted.

In a seventh aspect, this invention provides a set of sheets of a polymeric composition, the sheets being (i) composed of different compositions containing different amounts of optical additives, and (ii) being such that they can be formed into a self-supporting shell according to the first aspect of the invention. There can be, for example, at least 2, at least 3, at least 4, preferably at least 5, e.g. 5-20 identical samples of each of the different sheets.

In an eighth aspect, this invention provides a novel polymeric composition for use in the invention.

BRIEF DESCRIPTION OF THE DRAWINGS

The invention is illustrated in the accompanying drawings. The Figure shows the color ranges which are often observed for discolored teeth (area A), normal teeth (area B), whitened teeth (area C), orthodontic appliances (area D), and a preferred color range for tooth shells of this invention (area E). In the Figure, on the horizontal axis, the negative values relate to green colors and the positive values relate to red colors, and on the vertical axis, the negative values relate to blue colors and the positive values relate to yellow colors.

DETAILED DESCRIPTION OF THE INVENTION

In the Summary of the Invention above and in the Detailed Description of the Invention below, including the Examples and illustrations, reference is made to particular features of the invention. It is to be understood that the disclosure of the invention in this specification includes all possible combinations of such particular features. For example, where a particular feature is disclosed in the context of a particular aspect or a particular embodiment, that feature can also be used in combination with other particular aspects and embodiments, and in the invention generally, except where the context excludes that possibility. The invention disclosed herein include embodiments not specifically described herein and can for example make use of features which are not specifically described herein, but which provide functions which are the same, equivalent or similar to, features specifically disclosed herein.

The term "comprises" and grammatical equivalents thereof are used herein to mean that, in addition to the features specifically identified, other features are optionally present. For example, a composition or device "comprising" (or "which comprises") components A, B and C can contain only components A, B and C, or can contain not only components A, B and C but also one or more other components. The terms "consisting essentially of" and grammatical equivalents thereof are used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). The term "at most" followed by a number is used herein to denote the end of a range ending with that number (which may be a range having 1 or 0 as its lower limit, or a range having no lower limit, depending upon the variable being defined). When a range is given as " (a first number) to (a second number)" or "(a first number)—(a second number)", this means a range whose lower limit is the first number and whose upper limit is the second number. The terms "plural", "multiple", "plurality" and "multiplicity" are used herein to denote two or more than two features.

Where reference is made herein to "a" or "an" feature, this includes the possibility that there are two or more such features (except where the context excludes that possibility). Where reference is made herein to two or more features, this includes the possibility that the two or more features are replaced by a lesser number or greater number of features providing the same function, except where the context excludes that possibility. The numbers given herein should be construed with the latitude appropriate to their context and expression; for example, each number is subject to variation which depends on the accuracy with which it can be measured by methods conventionally used by those skilled in the art.

This specification incorporates by reference all documents referred to herein and all documents filed concurrently with this specification or filed previously in connection with this application, including but not limited to such documents which are open to public inspection with this specification.

Parts, percentages and ratios given in this specification are by weight unless otherwise noted.

Unless otherwise noted, the term color measurement is used herein to refer to measurements made using the LAB CIE color scale wherein L refers to total reflected light, A refers to the Red (+)—Green (−) color Axis and B refers the Yellow (+)—Blue (−) color axis measured using a D65 light source (daylight). However, color can also be measured using the CYMK scale which makes use of digital images. Other color measurement systems are known and any suitable method may be used in evaluating products of this invention.

The term pigment is used herein to denote a solid particulate coloring agent which can be mixed with a polymer.

The term dye is used herein to denote a coloring agent that is soluble or molecularly dispersed in a polymer.

The term fluorescent agent is used herein to denote a material that absorbs light in one region of the spectrum and emits light in the same or different region of the spectrum. The emission may be almost immediate or may be delayed.

The term light transmission is used herein to denote the amount of light passing through a sample. Unless otherwise stated, transmission refers to visible light as measured by a method similar to ASTM D1003-11 Standard Test Method for Haze and Luminous Transmittance of Transparent Plastics. Light transmission may also be measured using a colorimeter and a white reference sample, in which case the measurement includes two passages of light through the sample.

The term incident light is used herein to denote light which shines onto an object and which may be reflected, scattered or least partially absorbed by the object.

The term reflected light is used herein to denote incident light which reflects off the surface of an object after impinging on the object.

The term scattered light is used herein to denote light which diverges from a straight path after it has impinged on an object.

The term light scattering particles is used herein to denote particles having a size from about 0.2 to about 20µ and which are transparent or substantially white. By white is meant that the particles do not absorb significant amounts of light in the range from about 400 nm to about 700 nm.

The term thermoplastic polymer is used herein to denote a polymer which is relatively hard at a lower temperature, which becomes relatively soft when subjected to heat and pressure, and again becomes relatively hard when cooled, provided that the heat and pressure do not chemically decompose the polymer.

The term thermosetting polymer is used herein to denote a polymeric composition which is a solid or viscous material at a relatively low temperature and which, when subjected to heat and/or suitable radiation, and/or when the material undergoes one or more chemical reactions, changes irreversibly into an infusible polymer network. The term thermoset polymer is used to denote a cured thermosetting polymer.

The Polymer in the Polymeric Composition.

The polymer in the polymeric composition in the self-supporting shell used in the present invention can be a homopolymer, or a random, block or a graft copolymer. The composition can contain a single polymer or a mixture of two or more polymers. Generally, the polymer is substantially transparent, so that the optical characteristics of the self-supporting shell are dominated by the optical additives which are mixed with the polymer, but the invention includes the possibility that the polymer is a semicrystalline polymer which scatters light.

The polymer can optionally have one or more of the following characteristics (i.e. a single one of the following characteristics or any possible combination of two or more of the following characteristics).

(1) The polymer comprises a thermoplastic polymer.
(2) The polymer comprises a thermoset polymer.
(3) The polymer is an elastomer, preferably an elastomer having elongation to break greater than 200% and a 100% modulus of less than 3000 PSI (value for D50 or less TPU)
(4) The polymer is a polyester, for example a polyethylene terephthalate glycol polymer (PETG), e.g. one of the polyesters sold by Eastman Chemical under the trade names Eastar and Durastar, or one of the polyesters sold by DuPont under the trade name Hytrel.
(5) The polymer is a polyurethane, for example a rigid polyurethane such as that sold by Lubrizol Corporation under the trade name Isoplast, or a thermoplastic polyurethane (TPU) such as one of those sold by Lubrizol Corporation under the trade name Pellethane, by Merquinsa under the trade name Pearlthane, by BASF under the trade name Elastollan, and by Bayer under the trade name Texin.
(6) The polymer is a polyolefin, including high-density polyethylene, low density polyethylene, medium density polyethylene, linear low density polyethylene; a copolymer of ethylene and one or more comonomers, e.g. comonomers selected from the group consisting of other $\alpha$-olefins, vinyl acetate, acrylic acid, methacrylic acid, methyl acrylate, ethyl acrylate and butyl acrylate; polypropylene, e.g. clarified polypropylene; a propylene copolymer, e.g. a clarified propylene copolymer; polystyrene; a copolymer of styrene and one or more comonomers, e.g. comonomers selected from the group consisting of acrylic comonomers, acrylonitrile, acrylonitrile and butadiene, including block copolymers of styrene with ethylene, ethylene and propylene, isoprene and butadiene; polymers of cyclic olefins; and polymethyl pentene.
(7) The polymer is an acrylic or methacrylic resin, including polyacrylonitrile and copolymers of acrylonitrile.
(8) The polymer is an aliphatic or aromatic or mixed aliphatic aromatic polyamide, a polycarbonate, a polyether, an ionomer resin or a cellulose ester or ether.
(9) The polymer is a fluoropolymer, e.g. polyvinylidene fluoride, fluorinated ethylene propylene, polyvinyl chloride, or the product sold under the tradename Kynarflex.

The Additives in the Polymeric Compositions.

The polymeric composition can contain a single optical additive or a mixture of two or more optical additives. The polymeric composition can contain other additives which are not optical additives. The optical additives may be one or more optical additives selected from the group consisting of pigments, dyes, light scattering particles and fluorescent materials.

The optical additive can optionally have any one of the following characteristics, or any possible combination of one or more of the following characteristics.

(1) The optical additive, when dispersed in a sample of the polymeric composition having a thickness of 0.76 mm, preferentially absorbs light within the range from about 550 to about 700 nm, such that, when measured against a reference white sample (e.g. a white color tile) using conditions D 65, the LAB color values for the combination of the white color tile and the polymer sheet have an L value of between about 18 and 95, an A value from about −2 to +2 and a B value from about −1 to −10.

(2) The optical additive comprises a pigment or dye having a color which ranges from blue to violet, for example ultramarine blue, ultramarine violet, manganese oxides, phthalocyanine, violet 92, violet 11C, blue 385, blue 214, blue 30C591, blue 30C588, FDC blue #1, blue 214. Other blue and violet pigments which can be used include the following (which are listed by their CI name) PB 1, PB 1:2; PB 9, PB 15; PB 15:1, PB 15:2, PB 15:3, PB 15:4, PB 15:6, PB 15:34; PB 16, PB 17, PB 24, PB 25, PB 27, PB 28, PB 29, PB 30, PB 31, PB 34, PB 35; PB 36; PB 36:1, PB 60, PB 61, PB 61:1, PB 62, PB 63, PB 66, PB 68, PB 71, PB 72, PB 73, PB 74, PB 75, PB 76, PB 79, PB 80, PB 81, PB 82, PB 84, PB 128, PV 1, PV 1:1,PV 1:2, PV 2, PV 2:2, PV 3, PV 3:1, PV 3:3 PV 5, PV 5:1, PV 7, PV 13, PV 14, PV 15, PV 16, PV 18, PV 19, PV 23, PV 25, PV 27, PV 29, PV 31, PV 32, PV 36, PV 37, PV39, PV 42, PV 44, PV 47, PV 48, PV 49, PV 50, PV55, PV 58, and PV 17.

(3) The optical additive comprises a red pigment or die, for example NR 1. NR 2, NR 3, NR 4, NR 6, NR 8, NR 9, NR 10, NR 11, NR 12, NR 16, NR 20, NR 22, NR 23, NR 24, NR 25, NR 26, NR 28, NR 31, PR 1, PR 2, PR 3, PR 4, PR 5, PR 6, PR 7, PR 8, PR 9, PR 12, PR 13, PR 14, PR 15, PR 17, PR 19, PR 21, PR 22, PR 23, PR 31, PR 32, PR 38, PR 39, PR 47, PR 48, tPR 48:1, PR 48:2, PR 48:3, PR 48:4, PR 49, PR 49:1, PR 49:2, PR 52:1, PR 52:2, PR 53, PR 53:1, PR 57, PR 57:1, PR 57:2, PR 58:4, PR 60, PR 60:1, PR 61, PR 62, PR 63, PR 63:1, PR 69, PR 81, PR 81:1, PR 81:2, PR 81:3, PR 81:4, PR 83, PR 83:1, PR 83:3, PR 85, PR 88, PR 89, PR 90, PR 90:1, PR 101, PR 101:1, PR 102, PR 103, PR 104, PR 105, PR 106, PR 107, PR 108, PR 108:1, PR 109, PR 112, PR 113, PR 113:1, PR 114, PR 119, PR 120, PR 121, PR 122, PR 123, PR 139, PR 144, PR 146, PR 147, PR 148, PR 149, PR 150, PR 160, PR166, PR 168, PR 169, PR 170, PR 170:1, PR 171, PR 172, PR 173, PR 174, PR 175, PR 176, PR 177, PR 178, PR 179, PR 180, PR 181, PR 183, PR 184, PR 185, PR 187, PR 188, PR 190, PR 192, PR 193, PR 194, PR 200, PR 202, PR 204, PR 206, PR 207, PR 208, PR 209, PR 210, PR 211, PR 212, PR 213, PR214, PR 216, PR221, PR 223, PR 224, PR 226, PR 230, PR 231, PR 232, PR 233, PR 235, PR 236, PR 238, PR 239, PR 242, PR 243, PR 245, PR 251, PR 252, PR 253, PR 254, PR 255, tPR 256, PR 257, PR 258, PR 259, PR 260, PR 262, PR 264, PR 265, PR 266, PR 268, PR 269, PR 270, PR 271, PR 272, PR 273, PR 274, PR 275, PR 276, PR 279, PR 282, PR 286, PR 287, PR 288, and PR 571.

(3) The optical additive comprises light scattering (reflecting) particles, preferably light scattering particles which, when a sample of the polymeric composition having a thickness of 0.76 mm is exposed to natural light, from about 5% to about 50%, preferably 5 to 25%, of the incident light is reflected. Suitable light scattering particles include titanium dioxide, barium sulfate, calcium carbonate, boron nitride, silica, mica, and spherical glass particles. The presence of such an additive in the shell tends to mask the natural color of the teeth (which usually has a yellowish and/whole yellowish red tint) because a portion of the incident light is reflected before it is absorbed by the teeth. If the amount of reflected incident light is less than about 5%, the improvement is slight, whereas if the amount of reflected incident light is greater than about 50%, the perception of the underlying tooth structure may be reduced to a level such that the teeth are not perceived as natural.

Light scattering occurs when there is a difference between the refractive index of the particles and the polymer in which they are dispersed. The greater the difference in refractive index, the greater the degree of scattering. If the particles are transparent to the incident light in the wavelengths of interest, then essentially all of the light will be reflected or will pass through. If the particles absorb light in one or more ranges of wavelength, then the polymeric composition will be perceived as having a color which contains a reduced amount of those wavelengths. If the proportion of light reflecting particles is high and substantially all the incident light is scattered, the composition will appear white. At lower levels, the composition may appear translucent and light going through it will be "diffuse". For use in this application it is generally desired that any light scattering particles added do not absorb light, so they do not contribute to off color or increase of the grey value of the teeth. In some cases it is desirable to utilize particles that are sufficient to cause light scattering, while maintaining a high degree of total light transmission.

It has been found that appropriate use of light-scattering particles can not only result in teeth which look whiter, but can also mask areas of teeth having different colors, for example stained regions or darker areas near the base of the teeth, resulting in a more uniform and cosmetically desirable appearance.

(4) The optical additive comprises a fluorescent material which absorbs ultraviolet light having a wavelength of less than about 400 nm and which emits light in the range from about 400 to about 600 nm. These fluorescent materials are also referred to as brightening agents. Optionally the fluorescent material can also absorb light having a wavelength in the range from about 550 to about 700 nm. Dyes and/or pigments cause selective absorption of light such that the reflected light is more equally balanced across the visible spectrum (more equal amounts of each primary color); as a result, the presence of dyes and/or pigments in the shell make the perceived tooth color closer to white, but also reduces the total amount of light reflected, so that the teeth do not appear as bright. Fluorescent materials, by absorbing light outside the visible spectrum and emitting light in the purple-blue-green region of the visible spectrum, can make the teeth appear both whiter and brighter. Many fluorescent materials are known and have a wide range of chemical structures. They include for example triazine-stilbenes, coumarins, imidazolines, diazoles, triazoles, benzooxazolines and biphenyl-stilbenes. Specific optical brighteners include the materials designated by the CAS number 7128-64-5, 1533-45-5, 2397-00-4, 5089-22-5, 40470-68-6, 13001-38-2, 13001-39-3, 58449-88-0, 13001-40-6, 16470-24-9, 2226-96-2, 4193-55-9, 27344-41-8 and 16090-02-1.

Polymeric Compositions.

The polymeric composition in the self-supporting shells used in the present invention comprises a polymer, for example a polymer as disclosed above, and an optical additive, for example an additive as disclosed above. In some cases, it is preferable that the composition, when in the form of a uniform sheet having a thickness of 0.5 mm, has a total transmission of greater than about 80% and a diffuse transmission greater than about 50%, when measured by ASTM D 1003.

For the best results, which in most cases means teeth which are natural looking and as white as is desired by the individual whose teeth are being treated, the selection of the optical additives will be made in conjunction with inspection of the teeth onto which the shell it is to be placed. It is not at present practical to formulate a special composition for each individual. But it is practical to formulate a relatively limited number of "standard" compositions from which those skilled in the art, having regard to their own knowledge and the disclosure in this specification, will be able to select a composition which is likely to give excellent results.

Those skilled in dentistry are familiar with the ways in which the color of teeth can be assessed, and the selection of a material for a filling or a crown to match the natural color of teeth. Common tooth colors are often designated by a combination of a letter (usually A-D) and a number (usually 1-4), with A, B, C and D designating different hues (A red yellow, B yellow, C gray, and D red yellow gray), and 1-4 designating the color intensity. The designations M1, M2 and M3 are typically used to denote highly bleached teeth. Alternatively, the color of teeth can be measured by a colorimeter. Having determined the color of the teeth to be covered by the self-supporting shell, one skilled in the art will select a shell material which, when converted into a shell and placed over the teeth, will result in covered teeth which are perceived to have the desired color (which will normally be substantially whiter than the natural color of teeth), and which will preferably completely or partially disguise any staining of the teeth. For example, if a tooth having (on the VITA scale) a B 4 color is covered with a shell having (on the LAB scale) A and B values of 2.5 and -5, the tooth will appear from about 1 to about 4 shades lighter. It should be noted that the color of the shell material will not be the perceived color of the covered teeth, since the perceived color will depend on both the underlying natural color of the tooth, the color of the shell material and the type of incident illumination. Preferably the color of the natural teeth is at least one shade lighter is according to the VITA scale than the color of the same teeth without the shell Preparation of the Polymeric Compositions and of Polymeric Sheets Comprising Those Compositions.

The polymeric compositions used in this invention, and polymeric sheets comprising those compositions, can be prepared by conventional methods which are well-known to those skilled in the art of polymer technology.

Polymeric Sheets for Conversion into Self-Supporting Polymeric Shells

It will often be convenient for the self-supporting polymeric shells to be produced by shaping a polymeric sheet of a desired composition. The polymeric sheet can optionally have any one of the following characteristics, or any possible combination of one or more of the following characteristics.

1. It is a flat sheet having a uniform thickness of 0.10-2 mm, preferably 0.15-1.5 mm.
2. It is a flat sheet whose outer periphery is circular, oval or rectangular (including square), for example with an area of 10-100 in.$^2$
3. It is a flat sheet having dimensions such that it will completely cover a model of the teeth in the upper jaw or the lower jaw of an adult, or of a child, for example a flat sheet which is a circular disk, a flat sheet which is part (for example half) of a circular disk.
4. The polymeric composition is the same throughout the sheet.
5. The polymeric composition varies from top to bottom of the sheet. For example, the concentration of the additive (or one or more of the additives) is different at different levels going through the thickness of the sheet, including the possibility that there is no additive (or none of one or more of the additives) at one or more levels.

6. The sheet is a laminate having two or more layers of different polymeric compositions, for example (1) a laminate which contains an optical brightener in a layer which, when the sheet is formed into a self-supporting shell, is not part of the exterior surface of the shell, for example in a layer which is the central layer of a three layer laminate, or (2) a laminate which comprises (i) a first layer which, when the sheet is formed into a self-supporting shell, is in contact with the teeth, and which contains a first concentration of an optical additive, and (ii) a second layer which, when the sheet is formed into a self-supporting shell, is exposed, and which is free from the optical additive or which contains a second concentration of the optical additive, the second concentration being substantially less than the first concentration, for example not more than 0.2 times the first concentration. The polymers in the different layers are generally the same but can be different.
7. The sheet has a variable thickness such that when the sheet is thermoformed over a model of the teeth, each part of the thermoformed sheet has a thickness of at least 0.1 mm, at least 0.15 mm, at least 0.2 mm or at least 0.3 mm, and a thickness of at most 1.5 mm, preferably at most 1 mm., preferably a thickness in the range of 0.2 to 1.0 mm.
8. The sheet has a color within area E shown in the Figure.
9. The sheet contains substantially no fluorescent agent and has values of L, A and B on the LAB scale when the sheet is measured on a white color tile, as shown in the following table.

|  | L | A | B |
| --- | --- | --- | --- |
| Preferred | 75 to 99 | −3 to 6 | −10 to −1 |
| More preferred | 80 to 99 | −2 to 5 | −7 to −1 |
| Particularly preferred | 85 to 99 | −1 to 5 | −5 to −1.5 |

Since the value of L is the total light (L being 100), the added coloring agents will always reduce L to less than 100 if the sheet contains no fluorescent agent. In some embodiments, the sheet has a value of L greater than about 85, a value of A greater than about −0.5 and less than about 6.0, and a value of B from about −1.0 to −15.0.

10. The sheet contains a fluorescent agent and optionally other optical agents, and has values of L, A and B on the LAB scale when the sheet is measured on a white color tile, using a light source that includes light with a frequency of about 300 to about 400 nm (UV) and is filtered to D65, as shown in the following table.

|  | L | A | B |
| --- | --- | --- | --- |
| Preferred | 75 to 110 | −3 to 6 | −10 to −1 |
| More preferred | 80 to 110 | −2 to 5 | −7 to −1 |
| Particularly preferred | 85 to 110 | −1 to 4 | −5 to −1.5 |

In some embodiments, L is greater than about 85, A is −1.0 to 6.0, and B is −1.0 to −10.0, preferably −1.0 to −5.0.

11. The sheet has a transparency of greater than 75%, preferably greater than 85%.
12. The sheet is in the form of a roll, 5-6 inches (127-152 mm) wide, and 50-100 feet (15-30 m) long
13. A plurality of sheets, e.g. 20, 50, 100 or 500 sheets, are packaged together.
14. The sheet has a moisture content of less than 1%, preferably less than 0.5%.
15. The sheet is prepared by a process which comprises drying under control conditions which prevent discoloration of the sheet.

The Self-Supporting Polymeric Shells

The self-supporting shells can be prepared in any appropriate way. In one embodiment, the shell is prepared by shaping a sheet comprising the polymeric composition, for example by thermoforming the sheet over a model of the teeth to which the shell is to be fitted.

The First and Second Aspects of the Invention.

The self-supporting shell must fit closely to at least a major part of the front of the teeth over which it is placed, and preferably fits closely to a substantially the entire surface of the teeth over which it is placed. Generally, the shell will be one which can be removed by the wearer simply by pulling the shell off the teeth (which may be desirable for example when eating or for conventional tooth cleaning). However, the invention includes the possibility that the shell is secured to the teeth in some more permanent fashion.

The shell optionally has one of the following characteristics, or any possible combination of one or more of the following characteristics.

(1) The average thickness of the shell is at least 0.1 mm, preferably at least 0.15 mm, and at most 1.5 mm. When the only purpose of the shell is to change the appearance of the teeth, the average thickness is preferably at most 0.5 mm or at most 0.4 mm. When the shell is also used as part of an orthodontic procedure, for example a retainer or other dental appliance, the average thickness of the shell is greater, for example at least 0.5 mm or at least 0.6 mm.

(2) When the shell is prepared by thermoforming a polymeric sheet of uniform thickness, the thickness of the shell will vary from place to place, depending upon the amount of deformation of the sheet during the thermoforming process. When the only purpose of the thermoformed shell is to change the appearance of the teeth, it generally has a thickness which is at least 0.06 mm, at least 0.08 mm, at least 0.1 mm or, at least 0.2 mm, at least 0.3 mm, at least 0.4 mm at least 0.5 mm, at least 0.6 mm, or at least 0.7 mm, and a thickness of at most 1.0 mm or most 0.8 mm. When the thermoformed shell is also used as part of an orthodontic procedure, it generally has a thickness which is at least 0.5 mm, at least 0.6 mm, at least 0.7 mm, at least 0.8 mm, at least 0.9 mm, at least 1.0 mm, at least 1.1 mm, at least 1.2 mm, at least 1.3 mm, or at least 1.4 mm, and a thickness of at most 1.5 mm. When the only purpose of the shell is to change the appearance of the teeth, it preferably has a thickness in the range of 0.2 to 0.6 mm, particularly in the range of 0.3 to 0.5 mm. When the thermoformed shell is also used as part of an orthodontic procedure, it preferably has a thickness of the range of 0.3 to 1.0 mm, particularly in the range of 0.5 to 0.8 mm.

The shell can be prepared by thermoforming a polymeric sheet which is not of uniform thickness, for example a polymeric sheet which has a greater thickness in the areas which will be deformed by the thermoforming.

When the only purpose of the shell is to change the appearance of the teeth, the polymeric composition can have a flexural modulus of less than 1000 MPa or less than 800 MPa. When the shell is also used as part of an orthodontic procedure, the polymeric composition preferably has a flexural modulus of more than 1000 MPa, preferably more than 1500 MPa, e.g. 1000-3000 MPa.

(3) The polymeric shell comprises one or more optical additives. The concentration of the additives which modify the optical properties of the shell can be greater near the surface of the tooth than it is further from the surface of the tooth. For example, the polymer at the surface of the shell remote from the surface of the tooth can be substantially free of the optical additives. When the optical additive is uniformly dispersed in the shell, there is often a "fattening" effect which tends to make the teeth appear to extend to the outer surface of the shell. In an extreme case, where the outer surface of the shell is white and opaque, only the relatively flat outer surface of the shell is perceived, and the surface of the actual teeth is not perceived. In a preferred embodiment, the colored part of the shell would be no more than about 0.5mm thick, preferably no more than about 0.25 mm thick, and in some cases less than 0.1 mm.

(4) At least a portion of the shell has a total visible light transmission greater than about 75% and a LAB transmission value, when measured on a white tile, of L greater than or equal to 85, A from about −1.0 to about 6, preferably about −1 to about 3, and B from about −1.0 to about −15, preferably about −1.0 to −5.0.

(5) At least a portion of the thermoformed shell extends over the gum line beyond the upper or lower edge of the teeth. When the portion of the thermoformed shell which extends over the gum line has a total visible light transmission greater than about 75%, the portion of the shell that extends over the gum line is essentially not visible.

The Third Aspect of the Invention.

The third aspect of the invention preferably makes use of a polymeric composition which is selected by assessing the color of teeth over which the shell is to be fitted, the selection being made from a range of polymeric compositions of different colors. However, the invention includes the possibility that the composition is one of a number of "standard" colors. The assessment of the color of the teeth can be carried out by a dentist and the selection of the appropriate polymeric composition can be carried out by the dentist or by another party at a different location.

Any method can be used to make the selected polymeric composition into a shape which will fit over the teeth whose appearance is to be changed. Since the compositions cannot be shaped over the teeth themselves, the first step is to make a digital or physical image which corresponds to the teeth. A physical image can be made by forming an impression of the teeth, for example using an alginate composition, and then forming the physical image in the mold provided by the impression. A physical image can also be made from a digital image.

One method of making the self-supporting shell is to thermoform a sheet of the polymeric composition over a physical image of the teeth. Another method of making the self-supporting shell is to form the polymeric composition on the physical image of the teeth, for example by spraying, painting or deposition. The polymer can be a thermoplastic polymer or a thermosetting polymer which is cured, for example with ultraviolet light, after it has been formed into the desired shape.

Another method of making the self-supporting shell is to create it by a stereolithographic process (three dimensional printing) based upon a digital image of the teeth.

The Fourth Aspect of the Invention.

The fourth aspect of the invention includes the steps of (A) assessing the color of teeth over which the shell is to be placed, and (B) based on the assessment in step (A), selecting a composition from a range of compositions having different colors. The method can also include, as a preferred step, (C) forming the selected composition into a self-supporting shell. These steps can be carried out by the same person (usually a dentist); or each of the steps can be carried out by a different person; or steps A and B can be carried out by the same person (usually a dentist) and step C carried out by a different person; or step A can be carried out by one person (usually a dentist) and steps B and C carried out by a different person.

The Fifth Aspect of the Invention.

The fifth aspect of the invention is a method which comprises
  (A) selecting, from a set of colored samples, a sample which matches the color of teeth to be treated, and
  (B) correlating the selected sample with a polymeric composition which, when formed into a self-supporting shell and placed over the teeth will give the teeth a desired appearance.

In a first embodiment of the fifth aspect of the invention, the samples are (i) sized so that they can be placed against teeth within a human being's mouth, (ii) have a range of colors which correspond to the natural colors of teeth, and (iii) are correlated with different compositions containing different amounts of optical additives such that polymeric compositions correlated with the samples, when formed into self-supporting shells according to the first aspect of the invention, will give the teeth a desired appearance. The set of samples can be a known set of samples except that the samples are correlated with different compositions which when formed into a self-supporting shells, will give teeth a desired appearance. The set of samples can for example contain at least 2, at least 3, at least 4, at least 5, at least 6, at least 7, at least 8, at least 9, or at least 10, for example at least 20, e.g. 20-50 different samples. The set of samples can be supplemented by photographs or digital images which will show how the teeth will appear after they have been fitted with a shell made of the correlated polymeric composition.

In a second embodiment of the fifth aspect of the invention, the samples are thin colored polymeric strips which have a similar thickness to a self-supporting shell and a range of colors which are the same as the available colors for the self-supporting shells. These strips will show the human being a good simulation of the tooth color that will be obtained when a self-supporting shell made of the selected colored strip is placed over the teeth.

The Sixth Aspect of the Invention.

The sixth aspect of the invention provides a sheet of a polymeric composition for use in the method of the third or fifth aspect of the invention, for example by thermoforming the sheet around a physical model of the teeth over which the shell is to be fitted.

The Seventh Aspect of the Invention.

The seventh aspect of the invention provides a set of sheets of a polymeric composition, the sheets (i) being composed of different compositions containing different amounts of optical additives, usually compositions which are identical except for the content of the optical additives, and (ii) being such that they can be formed into a self-supporting shell according to the first aspect of the invention. There can be, for example, at least 2, at least 3, at least 4, preferably at least 5, e.g. 5-20 identical samples of each of the different sheets.

The Eighth Aspect of the Invention.

The eighth aspect of the invention provides novel polymeric compositions for use in the invention. The compositions can have some or all of the characteristics set out above.

Use of the Invention When a Tooth is Missing.

When a tooth is missing, the absence of the tooth is conventionally disguised by making a bridge which contains an artificial tooth (a so-called "pontic"). This invention provides an alternative way of compensating for the absence of a tooth. The shell can be formed with a section corresponding to the missing tooth, and the interior of that section of the shell can be partially or completely coated and/or filled with a filling material having substantially the same color as the natural teeth. It has been found that it is significantly easier to match the color of the filling material to the natural teeth when using a shell of this invention than it is to match the color of a pontic to the color of the natural teeth.

Use of the Invention to Provide Orthodontic as well as Cosmetic Improvements.

If desired, one or more parts of the self-supporting shell can be offset from the natural position of one or more teeth, so that when the shell is in place, it exerts a force on one or more teeth which moves the teeth in a desired direction, for orthodontic purposes. In this use, the shell needs to be more rigid than is necessary, or even desirable, for a shell which has only a cosmetic purpose. For example, for orthodontic appliance, it is desirable to use a polymeric sheet which, before being thermoformed, is 0.5 to 0.8 mm thick and for the polymeric composition to have a flexural modulus between 1000 and 3000 MPa.

EXAMPLES

Example 1

The compositions A-F of Table 1 were prepared from tinted and non-tinted rigid polyurethane. CPU 664 and Zendura A are tinted. Isoplast 2530 is not tinted.

| Composition | Thickness (millimeters) | L color | A color | B color |
|---|---|---|---|---|
| A-CPU 664 | 0.82 | 74.85 | 9.92 | −20.7 |
| B-CPU 664 | 0.28 | 88.4 | 4.46 | −9.01 |
| C-CPU 664 | 0.16 | 92.39 | 2.72 | −5.15 |
| D-Zendura A | 0.77 | 95.9 | 0.45 | −0.18 |
| E-Isoplast 2530 | 0.81 | 97.47 | −0.07 | 1.44 |
| F-Isoplast 2530 | 0.8 | 94.5 | −0.24 | 6.22 |
| Normal Tooth Range | | 68 | 0.5 | 15 |

Reference tooth colors for "normal range teeth" are taken from the literature

An impression was made of an individual's upper teeth using alginate and converted into a positive model using dental plaster. A sheet of polyurethane (composition C) having a thickness of 0.16 mm was thermoformed over the positive plaster model, trimmed and cleaned. A second shell was prepared using a longer heating cycle resulting in a slightly thinner shell. These shells are designated UB-1 and UB-2 respectfully.

The natural teeth of Individual A were examined in sunlight and were found to have the same color. The shell UB-1 was then applied only to the upper teeth, and the upper and lower teeth photographed in sunlight. When the upper shell of Example 1 was placed on the upper teeth it was observed that the upper teeth were significantly whiter than the lower teeth.

The shell UB-2 was applied only to the upper teeth of Individual A, and the upper and lower teeth photographed in sunlight.

Color analysis of the right incisor in the upper teeth of the shell UB-2 and the natural color of the right incisor was conducted using a computer drawing program and is reported in Table 2.

TABLE 2

Color of Right Incisor with and Without Shell

| | Color of Right Incisor | | | |
|---|---|---|---|---|
| | Cyan | Magenta | Yellow | Black |
| No shell | 0 | 11 | 24 | 8 |
| Shell | 0 | 14 | 16 | 16 |

It can be noted that the yellow value was reduced from 24 to 16. In this example the UB-1 shell slightly over-corrected the original tooth color. It is estimated that a preferable initial value for the tinted plastics sheet would have a LAB color value of approximately; L =97, A =1.0, B =−2.0

Example 2

Samples A-G as shown in Table 3 below were prepared by mixing Styrene co-polymer K Resin BK10 (Chevron Phillips, LLC) with the ingredients and amounts thereof shown in Table 3. The ingredient OB-1 in Table 3 is the optical brightener 2,2-(1,2-ethenediyldi-4,1-phenylene) bisbenzoxazole (Keystone Aniline Corporation). The ingredients were mixed in an internal mixer and pressed into sheets approximately 0.65 mm thick. The sheets were subsequently formed into shells as in Example 1 and applied to the upper teeth of Individual A.

TABLE 3

Composition of K-Resin Formulations.

| Sample | Designation | OB-1 (%) | Ultramarine Blue (%) | Ultramarine Violet (%) | Barium Sulfate | Titanium Dioxide |
|---|---|---|---|---|---|---|
| A | BM79-38-A | 0.01% | | | | |
| B | BM79-38-B | 0.01% | 0.01% | 0.05% | | |
| C | BM79-38-C | 0.02% | | | | |
| D | BM79-39-A | 0.015% | | | 1% | |
| E | BM79-39-B | 0.015% | | | 1% | 0.2% |
| F | BM79-39-C | | .005% | | | 0.03% |
| G | BM79-39-D | | .006% | | | 0.05% |

The color values of Individual A's right incisor when covered with Shells A, B and C, UB-1 and UB-2 and two controls (two separate measures of the color value of the Individual A's right incisor with no cover over it) were measured, and the results are shown in Table 4 below.

TABLE 4

Measured Color Values

|  | Control-1 | Control 2 | Control Av | Shell UB-1 | Shell UB-2 | Shell A | Shell B | Shell C |
|---|---|---|---|---|---|---|---|---|
| Cyan | 0 | 0 | 0 | 0 | 0 | 0 | 0 | 0 |
| Magenta | 12 | 11 | 11.5 | 14 | 8 | 11 | 10 | 12 |
| Yellow | 28 | 25 | 26.5 | 16 | 12 | 19 | 15 | 17 |
| Gray | 11 | 15 | 13 | 16 | 7 | 12 | 12 | 12 |
| Total CYMK | 51 | 51 | 51 | 46 | 27 | 42 | 37 | 41 |

The shell prepared from composition E was opaque (<50% light transmission) and judged to be less desirable as a tooth whitening shell as the opacity of the shell masks the spaces between the teeth such that individual teeth are not as apparent as desired. However, the shell of composition E has value when it is desired to mask the absence of a tooth, such as when a pontic is used.

The shell prepared from composition G (BM 79-39-D) was evaluated in bright daylight and in diffuse light, and the results are shown in Table 5. As would be expected, the specific colors values vary with type and amount of light. Table 5 shows the color values of Individual A's right incisor when covered with shell prepared from composition G, and the control (the color value of the Individual A's right incisor with no cover over it).

TABLE 5

Evaluation of Shell From Composition BM79-39-D

|  | Control-Sun | Bm79-39-D Sun | Control Shade | BM79-39-D Shade |
|---|---|---|---|---|
| Cyan | 0 | 0 | 0 | 0 |
| Magenta | 15 | 7 | 24 | 18 |
| Yellow | 23 | 14 | 49 | 28 |
| Gray | 19 | 12 | 28 | 34 |

The color data in both types of lighting show a dramatic reduction in yellowing and improvement in tooth color.

Example 3

PETG resin (Eastar 6763) is combined with ultramarine blue and ultramarine violet pigment master batch and extruded into a sheet of thickness 0.07 mm the amount of the pigment being such that the sheet has LAB color values measured on a white color tile of L=94, A=1.3, B=−2.5. A dental impression is made from an individual's upper and lower teeth using a plastic dental tray and alginate resin. Dental stone is prepared by mixing 100 grams of plaster with 24 grams of water and poured into the alginate mold and allowed to set. The plaster model is removed and cleaned. Disks are prepared from the extruded sheet by die cutting samples 125 mm in diameter and dried at 80 C. for 2 hours. The dried discs are pressure-formed over the plaster models using a Biostar® thermoformer manufactured by distributed by Great Lakes Dental. The thermoformed parts are removed from the plaster models, trimmed to the gum line and cleaned. Color measurements are made on the individual's teeth before and after the shells are placed over the teeth.

The following statements define particular aspects of the invention.

Statement 1. A shell which is composed of a polymeric composition containing an optical additive and which contains cavities shaped to cover a plurality of teeth, the shell having an average thickness of from 0.1 mm to 1.5 mm, preferably 0.2 to 1.5 mm, and a transparency of greater than 75%, preferably greater than 85%, the observed color of the teeth when they are covered by the shell (i) being substantially less yellow than the color of the teeth without the shell, and/or (ii) the observed color of teeth when they are covered by the shell being at least one shade lighter, according to a tooth color classification system, than the color of the same teeth without the shell, and/or (iii) the observed color of the teeth when they are covered by the shell being brighter than the color of the same teeth without the shell.

Statement 2. A shell according to Statement 1 wherein the polymeric composition is based on a polymer selected from the group consisting of polyolefins, e.g. polyethylene, polyesters, including for example copolymers such as polyethylene terephthalate glycol resins (PETG), polyurethanes including rigid polyurethanes, thermoplastic polyurethanes (TPU), polypropylene and propylene copolymers, acrylic and methacrylic resins and co-polymers, polystyrene and co-polymers including random and block co-polymer and elastomers and fluoropolymers.

Statement 3. A shell according to Statement 1 or Statement 2 wherein the optical additive comprises one or more of a pigment, a dye, light scattering particles and a fluorescent material with optical properties.

Statement 4. A shell according to Statement 1 or Statement 2 wherein the optical additive is selected from the group consisting of ultramarine pigments, ultramarine blue, ultramarine violet, cobalt-based pigments and resin soluble dyes.

Statement 5. A shell according to Statement 1 or Statement 2 wherein the optical additive comprises a material selected from the group consisting of titanium dioxide, barium sulfate, calcium carbonate, silica, mica and zinc oxide.

Statement 6. A shell according to Statement 1 or Statement 2 wherein the optical additive comprises a fluorescent material which absorbs light with a wavelength of less than 390 nm and emits light with a wavelength of from 400 nm to 600 nm.

Statement 7. A shell according to Statement 1 or Statement 2 wherein the optical additive comprises a fluorescent material and a pigment or dye that absorbs light in the range of from about 550 nm to about 700 nm.

Statement 8. A shell according to any one of Statements 1 to 5 which does not contain a fluorescent agent and which, when not fitted over teeth, and measured on the LAB scale on a white color tile, has an L value from 50 to 99, preferably 75 to 99, more preferably 80 to 99, particularly preferably 85 to 99, an A value of -1 to 10, preferably -3 to 6, more preferably -2 to 5, particularly preferably -1 to 5 e.g. 0.5 to 5, and a B value of -1 to -14, preferably -10 to -1, e.g. -10 to -2, more preferably -7 to -1, particularly preferably -5 to -1.5.

Statement 9. A shell according to any one of Statements 1-7 wherein the optical additive comprises a fluorescent agent and which, when not fitted over the teeth, and measured on the LAB scale on a white color tile and using a light source that includes light with a frequency of about 300-400 nm filtered to D65, has an L value from 75 to 110, preferably 80 to 110, more preferably 85 to 110, particularly preferably 85 to 99, an A value of -3 to 6, more preferably -2 to 5, particularly preferably -1 to 4, and a B value of -10 to -1, more preferably -7 to -1, particularly preferably -5 to -1.5.

Statement 10. A shell according to any one of Statements 1-9 wherein from about 10% to about 50% of the incident light is reflected from the shell rather than the underlying tooth.

Statement 11. A shell according to any one of Statements 1-10 wherein the shell provides orthodontic treatment to the teeth.

Statement 12. A shell according to any one of Statements 1-11 wherein the shell comprises two or more layers, and the outermost layer contains a lower concentration of optically active materials than another layer.

Statement 13. A shell according to Statement 12 wherein the outermost layer is 0.2 to 0.7 mm thick Statement 14. A sheet of a polymeric composition which can be thermoformed into a shell according to any one of Statements 1-13.

The invention claimed is:

1. A self-supporting shell which (i) fits over one or more teeth and (ii) has been prepared by thermoforming a sheet over a model of the tooth or teeth, wherein said shell comprises a polymeric composition comprising a polymer and one or more optical additives and,
   (A) the one or more optical additives comprises light-scattering particles selected from the group consisting of one or more of titanium dioxide, barium sulfate, calcium carbonate, boron nitride, silica, mica and zinc oxide, and
   (B) (i) the shell comprises an outermost layer and one or more additional layers,
   (ii) at least one of the additional layers contains a first concentration of the one or more optically active additives, and
   (iii) the outermost layer contains a second concentration of the one or more optically active additives, the second concentration being less than the first concentration.

2. A self-supporting shell according to claim 1 wherein the one or more optical additives comprises a fluorescent agent which (i) absorbs light at frequencies below about 400 nm and (ii) emits light having frequencies between about 400 and about 600 nm.

3. A self-supporting shell according to claim 1 wherein the one or more optical additive comprises an additive selected from the group consisting of one or more of ultramarine blue, ultramarine violet, manganese oxides, cobalt-based pigments, resin-soluble dyes, phthalocyanine, Violet 92, Violet 11 C, blue 385, blue 214, blue 30 C5 91, blue 30 C588, FDC blue #1 and blue 214.

4. A self-supporting shell according to claim 1 wherein the sheet contains no fluorescent agent and before it is thermoformed, when it is measured on the LAB scale on a white color tile, and using a light source that includes light with a frequency of about 300-400 nm filtered to D65, has an L value from 75 to 99, an A value of -3 to 6, and a B value of -10 to -1.

5. A self-supporting shell according to claim 1 which has a thickness of at least 0.3 mm.

6. A self-supporting shell according to claim 1 wherein
   (i) the sheet is a laminate comprising an outermost layer and one or more additional layers,
   (ii) the additional layer, or each of the additional layers if there is more than one additional layer, contains the one or more optically active additives, and
   (iii) the outermost layer does not contain any optically active additives.

7. A self-supporting shell which (i) fits over one or more teeth, and (ii) has been prepared by thermoforming a sheet over a model of the tooth or teeth wherein said shell comprises a polymer and one or more optical additives, and
   (A) the one or more optical additives comprises a fluorescent agent which (i) absorbs light at frequencies below about 400 nm and (ii) emits light having frequencies between about 400 and about 600 nm, and
   (B) (i) the shell comprises an outermost layer and one or more additional layers,
   (ii) at least one of the additional layers contains a first concentration of the one or more optically active additives, and
   (iii) the outermost layer contains a second concentration of the one or more optically active additives, the second concentration being less than the first concentration.

8. A self-supporting shell according to claim 7 wherein the one or more optical additives comprises an additive selected from the group consisting of one or more of ultramarine blue, ultramarine violet, manganese oxides, cobalt-based pigments, resin-soluble dyes, phthalocyanine, Violet 92, Violet 11 C, blue 385, blue 214, blue 30 C5 91, blue 30 C588, FDC blue #1 and blue 214.

9. A self-supporting shell according to claim 7 wherein the sheet, before it is thermoformed, when it is measured on the LAB scale on a white color tile, and using a light source that includes light with a frequency of about 300-400 nm filtered to D65, has an L value from 75 to 110, an A value of -3 to 6, and a B value of -10 to -1.

10. A self-supporting shell according to claim 7 wherein
    (i) the sheet is a laminate comprising an outermost layer and one or more additional layers,
    (ii) the additional layer, or each of the additional layers if there is more than one additional layer, contains the one or more optically active additives, and
    (iii) the outermost layer does not contain any optically active additives.

11. A self-supporting shell which (i) fits over one or more teeth and (ii) has been prepared by thermoforming a sheet over a model of the tooth or teeth wherein said shell comprises a polymer and one or more optical additives, and
    (A) the one or more optical additives comprises an additive selected from the group consisting of one or more of ultramarine blue, ultramarine violet, manganese oxides, cobalt-based pigments, resin-soluble dies, phthalocyanine, Violet 92, Violet 11 C, blue 385, blue 214, blue 30 C5 91, blue 30 C588, FDC blue #1 and blue 214, and
    (B) (i) the shell comprises an outermost layer and one or more additional layers,
    (ii) at least one of the additional layers contains a first concentration of the one or more optically active additives, and (iii) the outermost layer contains a second concentration of the one or more optically active additives, the second concentration being less than the first concentration.

12. A self-supporting shell according to claim 11 wherein (i) the sheet is a laminate comprising an outermost layer and one or more additional layers, (ii) the additional layer, or each of the additional layers if there is more than one additional layer, contains the one or more optically active additives, and (iii) the outermost layer does not contain any optically active additives.

* * * * *